(12) United States Patent
Chudoba et al.

(10) Patent No.: US 7,543,519 B2
(45) Date of Patent: Jun. 9, 2009

(54) DEVICE FOR HIGH-PRECISION GENERATION AND MEASUREMENT OF FORCES AND DISPLACEMENTS

(75) Inventors: Thomas Chudoba, Dresden (DE); Volker Linss, Jena (DE)

(73) Assignee: ASMEC Advanced Surface Mechanics GmbH, Radeberg (DE)

(*) Notice: Subject to any disclaimer, the term of this patent is extended or adjusted under 35 U.S.C. 154(b) by 589 days.

(21) Appl. No.: 11/339,226

(22) Filed: Jan. 25, 2006

(65) Prior Publication Data

US 2006/0243079 A1 Nov. 2, 2006

(30) Foreign Application Priority Data

Jan. 25, 2005 (DE) .................. 10 2005 003 830

(51) Int. Cl.
*G05G 11/00* (2006.01)
(52) U.S. Cl. .................. 74/490.09; 74/490.12; 73/81
(58) Field of Classification Search .............. 74/490.13, 74/490.08, 490.09, 490.11, 490.12; 73/81
See application file for complete search history.

(56) References Cited

U.S. PATENT DOCUMENTS

| | | | |
|---|---|---|---|
| 4,400,970 A | 8/1983 | Ali et al. | |
| 4,435,976 A | 3/1984 | Edward, Jr. et al. | |
| 4,841,764 A | 6/1989 | Fischer | |
| 5,051,594 A * | 9/1991 | Tsuda et al. | 250/442.11 |
| 5,067,346 A | 11/1991 | Field | |
| 5,520,733 A * | 5/1996 | Doi et al. | 118/256 |
| 5,576,483 A | 11/1996 | Bonin | |
| 5,616,857 A | 4/1997 | Merck, Jr. et al. | |
| 5,661,235 A | 8/1997 | Bonin | |
| 6,050,139 A | 4/2000 | Bousfield et al. | |
| 7,316,155 B2 * | 1/2008 | Chudoba et al. | 73/81 |
| 2002/0062678 A1 | 5/2002 | Ahn et al. | |
| 2004/0011119 A1 | 1/2004 | Jardret et al. | |

FOREIGN PATENT DOCUMENTS

| | | |
|---|---|---|
| DE | 31 28 537 A1 | 2/1983 |
| DE | 34 08 554 A1 | 9/1985 |
| DE | 37 21 525 A1 | 3/1988 |
| DE | 37 37 910 | 5/1989 |
| DE | 37 38 106 A1 | 5/1989 |
| DE | 42 10 599 | 10/1993 |
| DE | 42 20 510 A1 | 12/1993 |
| EP | 1 092 142 | 4/2001 |
| JP | 2001 050882 | 2/2001 |
| JP | 2004 020375 | 1/2004 |

OTHER PUBLICATIONS

German Office Action in Application No. 10 2005 003 830.1, dated Oct. 5, 2005 with English translation.
European Office Action in Application No. 06 001 411, dated Oct. 6, 2006 and European Search Report with English translation.

* cited by examiner

*Primary Examiner*—David M Fenstermacher
(74) *Attorney, Agent, or Firm*—Collard & Roe, P.C.

(57) ABSTRACT

A device for high precision generation and measurement of forces (both pressure and tension) and displacements along a single axis includes a shaft for transferring the forces along an axis X. At least two biased first leaf springs are attached to the shaft and clamped at each end. The device has great rigidity in an axis Y perpendicular to the axis X in which the forces and displacements are generated.

20 Claims, 5 Drawing Sheets

DEVICE FOR HIGH-PRECISION GENERATION AND MEASUREMENT OF FORCES AND DISPLACEMENTS

CROSS REFERENCE TO RELATED APPLICATIONS

Applicants claim priority under 35 U.S.C. §119 of GERMAN Application No. 10 2005 003 830.1 filed on Jan. 25, 2005.

BACKGROUND OF THE INVENTION

1. Field of the Invention

The invention relates to a device for high-precision generation and measurement of forces and displacements.

2. Description of the Prior Art

High-precision generation and measurement of forces and displacements along an axis are generally used in the production of nano-indenters and scratch or wear testers. Forces and displacements in such devices are generated in different ways, according to the state of the art, whereby as a rule, only great rigidity of the moved shaft in the movement direction is a matter of concern.

Force and/or displacement can be generated and/or measured electrically (for example, electrostatically or capacitatively), magnetically, mechanically, or by means of a combination of the aforementioned methods. Simple methods for determining displacements and forces, such as optical reading of the displacement of a glass scale, and the use of a force measurement cell are described in the U.S. Pat. No. 5,616,857. Such methods, however, are only suitable for sufficiently large paths and forces. Another method is described in DE 3738106, wherein the force is generated by means of the current flowing through a coil which is situated in a field produced by permanent magnets. In this connection, the electric current is a measure of the force that is generated. However, the reproducibility is dependent on the constancy of the magnetic field of the permanent magnets.

A magnetic system is also described in DE 3408554. This system is in the form of a rotary magnet, which moves a lever arm that transfers a force to a substrate. Again, the electric current through the magnet serves as a measure of the force. In this system, however, the bearings can influence the accuracy and reproducibility of the force transfer.

DE 3128537 also describes a system wherein force is generated by way of a lever. A lever arm is moved using a cam. The determination of the transferred force takes place by way of an elongation measurement strip that is attached to an elastic part of the force transfer arm, while the path measurement takes place by means of a sensor on the shaft of the measurement device. Elongation measurement strips, however, have a poor signal/noise ratio for small signals. Significantly greater precision is possible using capacitative measurements, as they are described, for example, in U.S. Pat. Nos. 5,576,483 and 5,661,235. As described in these references, generation and measurement of path and force take place by way of electric voltages. In particular, the change in capacitance of a capacitor at a variable distance between its plates, or the change in the distance between the plates with a variable applied voltage is utilized.

According to U.S. Pat. No. 5,661,235, this system can be utilized for detecting forces and displacements in multiple directions. However, the forces that can be generated are on the order of 10 mN, and this is a significant disadvantage. Furthermore, the work is carried out using voltages of more than 100 V, which presents the risk of electric blowout. This would cause the force generation to become unusable. Furthermore, the suspension of the substrate holder must be electrically insulating, so that the internally used voltage does not reach the outside.

U.S. Pat. No. 5,067,346 describes the generation and measurement of forces and displacements by means of leaf springs that are clamped in on one side and not biased. Here, a disadvantage is the low rigidity in a direction perpendicular to the force and displacement being generated.

DE 37 21 525 A1 describes a microhardness testing device wherein a force-transferring shaft is attached to two membrane springs disposed in a force measurement housing. The membrane springs are perforated, held at their circumference and configured to be wave-shaped at their free side edges The shaft is movable and guided in the axial direction.

DE 42 20 510 A1 describes a device for setting a measurement tip onto a substrate, wherein the measurement tip is disposed on a vertically movable carrier. The carrier is clamped in place between two leaf springs, which are attached to a base body. A similar device is described in EP 1092142 B1, wherein a penetration body is disposed to be movable in one degree of freedom, by way of a penetration body holder attached to leaf springs.

In the case of the three solutions described above; however, a defined bias force of the membrane springs or leaf springs is not adjustable, and thereby each of the systems demonstrates insufficient rigidity.

SUMMARY OF THE INVENTION

One object of the invention is to provide a device for high-precision generation and measurement of forces and displacements, which has a high rigidity perpendicular to the axis in which the forces and displacements are being generated. Such a device according to an embodiment of the invention has a relatively simple structure, and provides great reliability and reproducibility of the forces and displacements being generated and measured.

This object is accomplished by a device according to an embodiment of the invention described herein. Advantageous embodiments are also described.

According to an embodiment of the invention, a device for high-precision generation and measurement of forces and displacements in a single-axis direction (both pressure and tension) has great rigidity in an axis Y perpendicular to an axis X, in which the forces and displacements are being generated. The device includes a shaft for transferring force, wherein the force-transferring shaft is attached to at least two first leaf springs that are biased and are clamped in on both sides. The first leaf springs are biased in a direction towards the Y axis and the bias is adjustable by way of at least one first bracing or clamping element.

The first leaf springs are preferably biased in a closed frame in the direction toward the Y axis. The frame may be movably mounted on a rack by means of at least two leaf springs lying opposite one another.

The force-transferring shaft may be disposed on at least one double pair of first leaf springs that are clamped in on both sides, wherein the first leaf springs can be deflected in the X direction. The first leaf springs may be hinged in a closed frame, under bias. The frame may be mounted to be movable in the X direction. The frame may also be mounted on two double pairs of second leaf springs that lie opposite one another.

In another embodiment, the frame may be movable in the X direction by means of four third leaf springs that are clamped in on one side. To implement the movement in the X direction, the frame may be coupled with a movement element by means of a connecting shaft. The movement element can move the frame in both a pulling direction and a pushing direction. The movement element may be configured as a piezoelectric element.

In another embodiment of the invention, the force-transferring shaft includes a device for measuring force and/or a device for measuring path, wherein it is possible to carry out the determination of the force by way of a path measurement. The device for measuring force may comprise a first LVDT (linear variable displacement transformer) transducer and the device for measuring path may comprise a second LVDT (linear variable displacement transformer) transducer. The force and/or path may additionally or alternatively be measured optically.

According to another embodiment of the invention, the force-transferring shaft can be coupled with a damping unit that acts in the axis X. The damping unit may comprise an oil bath into which a damping element rigidly attached to the force-transferring shaft is submerged, or an eddy current brake, wherein an aluminum or copper sheet is rigidly connected with the force-transferring shaft and positioned between two magnets.

The bias of the first leaf springs preferably takes place by means of first bracing elements, in a direction Y perpendicular to the X direction. For this purpose, the first bracing element has a first clamping strap and a first clamping plate, between which one end of a first leaf spring can be clamped in place by means of a first adjusting screw. The first clamping plate can then be adjusted or tightened against the frame in the Y direction, by means of a first straining screw, so that the clamped first leaf spring is biased in its longitudinal (Y) direction. The other end of the first leaf spring may be attached to the frame in non-adjustable manner, for example by means of a clamping element.

The bias of the second leaf springs takes place, for example, by means of second bracing elements in a direction Y perpendicular to the X direction, against the rack or frame. In the latter case, the second bracing element may include a second clamping strap and a second clamping plate, between which one end of a second leaf spring is clamped in place by means of a second adjusting screw. The second clamping plate can now be adjusted or tightened against the rack, in the Y direction, by means of a second straining screw, so that the clamped second leaf spring is biased in its longitudinal (Y) direction.

One advantage of a device according to an embodiment of the invention is that forces and displacements in one direction (for example, an X direction) are reliably generated and, at the same time, measured, by means of leaf springs that are clamped in on both sides and biased in a longitudinal (Y) direction. Embodiments of the invention can be used for high-precision generation and measurement of very small forces, and also for greater forces and displacements. Furthermore, a plurality of devices according to embodiments of the invention can be combined such that forces and displacements can be generated and measured in several directions.

Because the generation and measurement of the forces and displacements are conducted mechanically, the device is not susceptible to electromagnetic interference, and the substrate holders do not have to be electrically insulating.

A further advantage of a device according to an embodiment of the invention is that the device is very rigid in a direction perpendicular to the generated force/displacement (in the Y direction) because of the bias of the leaf springs, so that no displacement that acts in this perpendicular direction occurs, i.e. a force that acts in this direction cannot result in a displacement.

BRIEF DESCRIPTION OF THE DRAWINGS

Other benefits and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE INVENTION

Figure 1:
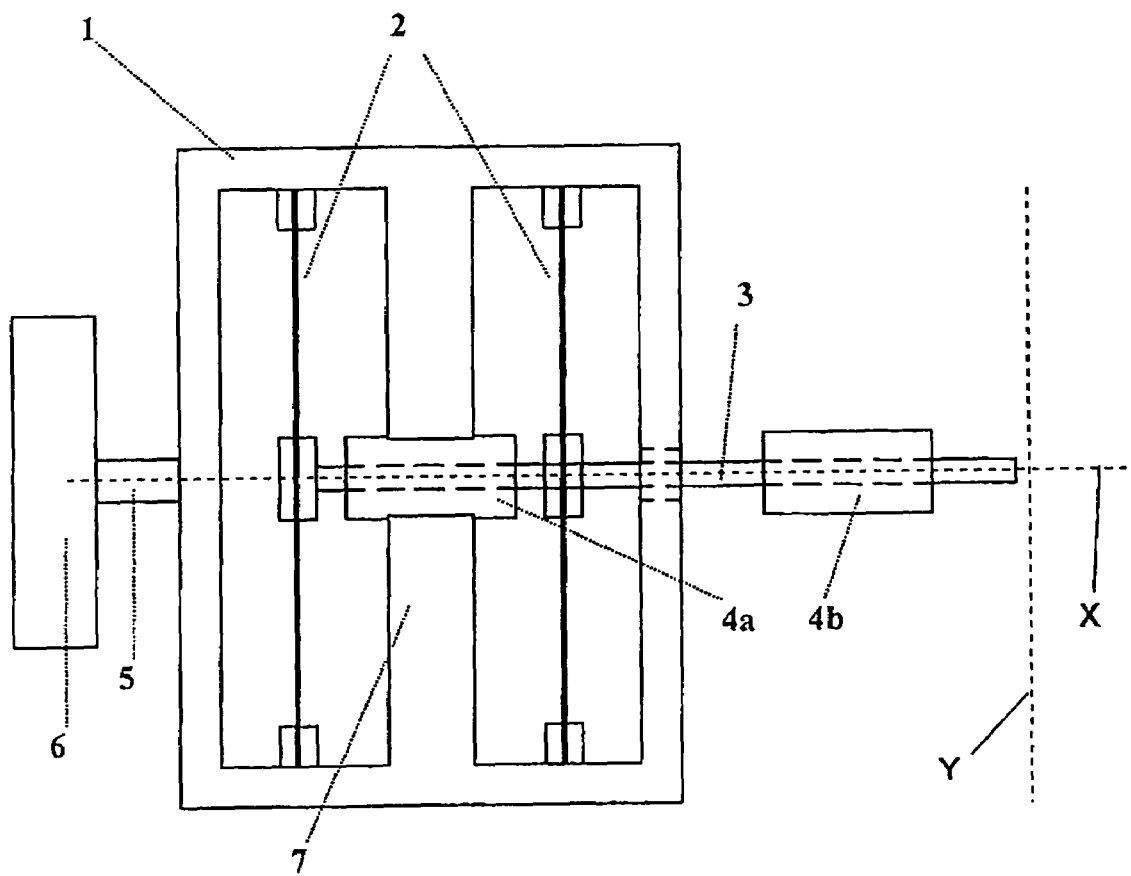
FIG. 1 shows a diagram of an embodiment of the invention.

The principle of the invention may be explained in greater detail with reference to FIG. 1. At least one double pair of leaf springs 2 is attached at their short ends, in a rigid, closed frame 1, and tensed in a vertical direction. Leaf springs 2 are rigidly connected with a force-transferring shaft 3, in the direction of which (X axis) the generation of force and/or displacement occurs (both pressure and tension).

Two ferrite cores of LVDTs 4a, 4b are rigidly attached to the force-transferring shaft 3. One LVDT 4a is for measuring force and is connected with the closed frame 1 with a rigid holder 7. A second LVDT 4b is rigidly connected with an external reference body, which serves as a reference point for the measurement of the displacement of the shaft 3.

Frame 1 may be connected with a movement element, such as a piezoelectric element 6, by way of a connecting shaft 5. The movement element can move the frame 1 back and forth in the longitudinal direction along the axis X of shaft 3.

LVDT 4b measures a position of shaft 3 with great precision. If a force acts on the shaft 3, in its longitudinal direction, deflection of the leaf springs 2 occurs, and this results in a displacement of the shaft 3 in the X axis, relative to LVDT 4a. This deflection is proportional to the force for sufficiently small forces, so that the signal produced by LVDT 4a can be calibrated to the force. In the direction of the longitudinal expanse of the first leaf springs 2, which lies perpendicular to the axis X, high rigidity of shaft 3 is achieved in an axis Y.

Figure 2:
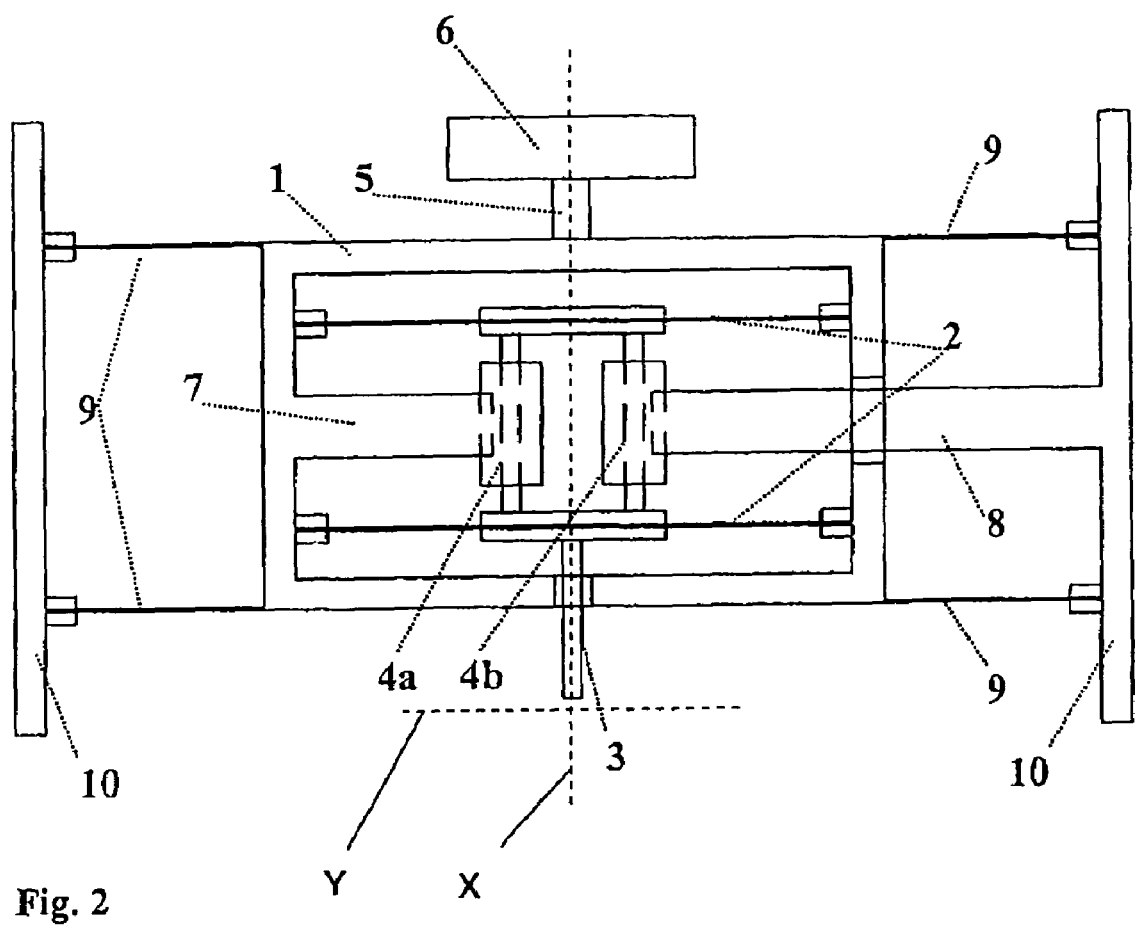
FIG. 2 shows an embodiment of the invention suspended for generation/measurement of vertical forces and displacements.

An exemplary embodiment of the invention is shown in FIG. 2. The closed frame 1 is suspended on a rack 10, via biased second leaf springs 9, to be movable in the direction of the axis X. LVDT 4a for measuring force is, again, attached to the frame 1 by way of a rigid connection 7. LVDT 4b for measuring displacement is fixed in place on rack 10 by way of a rigid connection 8, to measure displacement along the axis X.

In this embodiment, an indenter tip, for example, can be attached to shaft 3, such that displacement of the tip in the vertical direction and the force acting on it are measured. Displacement may be brought about via a piezoelectric element 6, which moves frame 1 and with it shaft 3 in the direction of the X axis. Likewise, a wire, a fiber, or a similar body for a tensile test can be clamped to shaft 3. In this embodiment active piezoelectric element 6 moves frame 1 upward. By mounting shaft 3 on leaf springs 2 and mounting frame 1 on second leaf springs 9, displacement of shaft 3 in the lateral (Y) direction is prevented or very greatly restricted.

Figure 3:
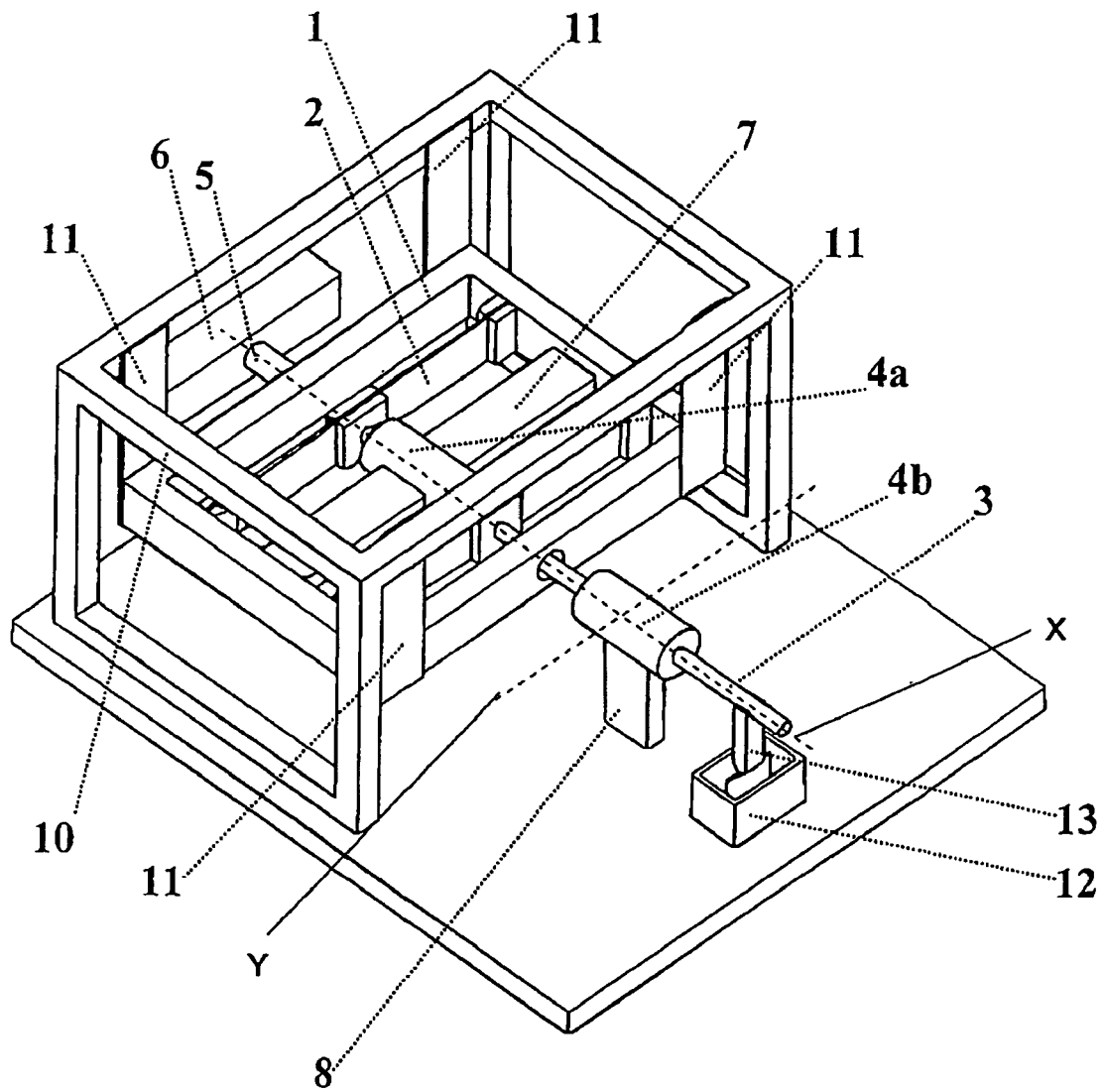
FIG. 3 shows an embodiment of the invention suspended for generation/measurement of horizontal forces and displacements.

Another exemplary embodiment is shown in FIG. 3. Here, generation and measurement of the force and displacement takes place in the horizontal direction (axis X), and a high degree of rigidity is provided in the direction of the axis Y. In this example, frame 1 is suspended on a rack 10 via four third leaf springs 11, and shaft 3 has its longitudinal direction in the horizontal position. A first LVDT 4a for measuring force is, again, attached to frame 1 via a rigid connection 7. A second LVDT 4b for measuring displacement is affixed to a base plate, which in turn holds rack 10 via a rigid connection 8.

In this exemplary embodiment, a damping element 13 may be fixed in place on shaft 3, which submerges into a damping unit in the form of an oil bath 12 and damps vibrations in the direction of the longitudinal axis of shaft 3. Such damping can also be provided in the example according to FIG. 2. If these vibrations are intentional, and are to be generated via the active piezoelectric element 6, the damping unit can be removed. Shaft 3 can be moved both back and forth in the direction of its longitudinal axis. Likewise, forces can be generated both in the compressive and tensile directions. A high degree of rigidity is achieved in the direction of the axis Y.

Figure 4:
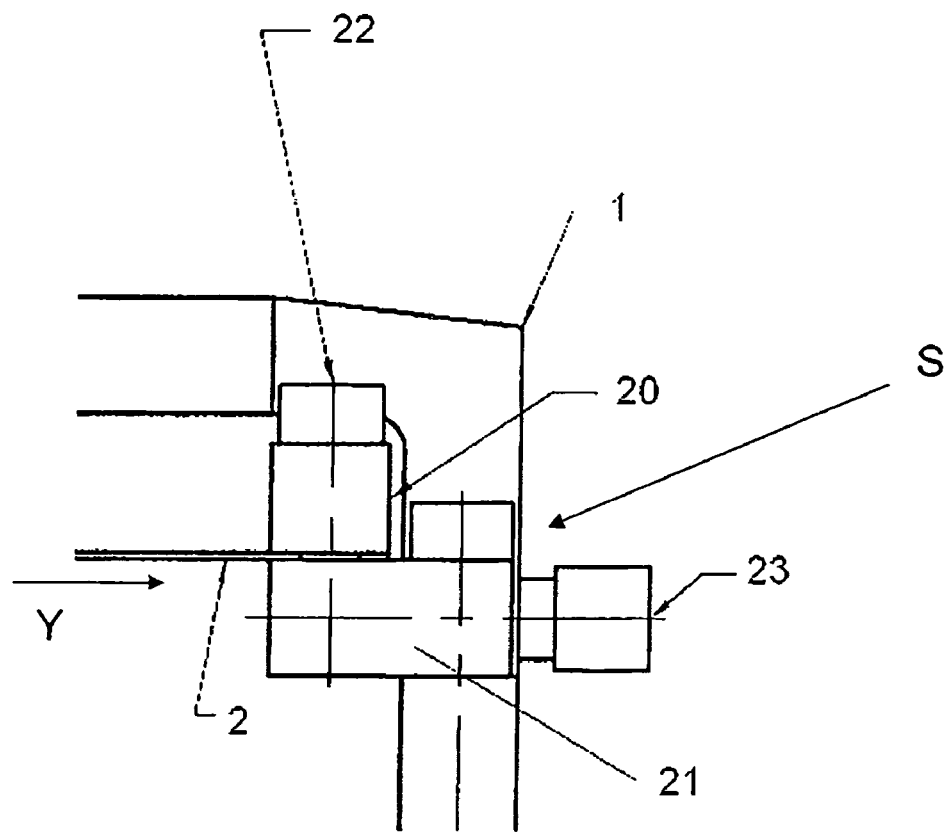
FIG. 4 shows a side view of an embodiment of the invention with an attachment of a first leaf spring on the frame.
Figure 5:
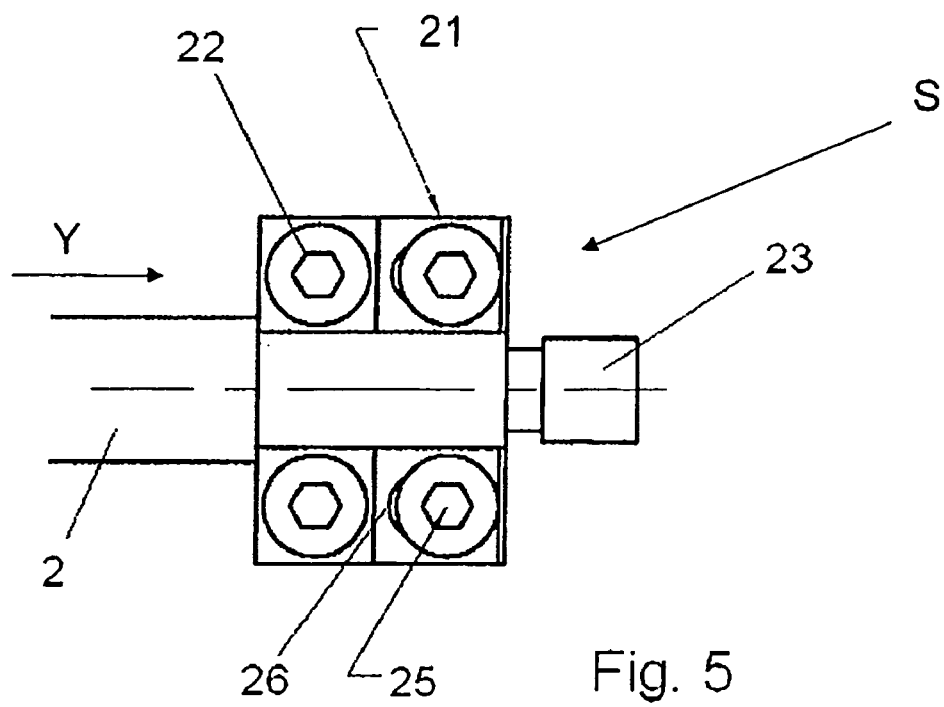
FIG. 5 shows a top view of the embodiment shown in FIG. 4.

FIG. 4 shows a side view of an embodiment wherein a first leaf spring is attached to the frame and FIG. 5 shows the same embodiment in a top view.

First bracing element S, which can generate a bias of first leaf spring 2 in the Y direction, includes a first clamping strap 20, a first clamping plate 21, a first adjusting screw 22, and a first straining screw 23. One end of first leaf spring 2 is clamped in place between first clamping strap 20 and first clamping plate 21, by means of first adjusting screw 22. Clamping plate 21 is braced against frame 1 by means of first straining screw 23, biasing first leaf spring 2 in its longitudinal direction (Y direction) when first straining screw 23 is tightened. First clamping plate 21 can be positioned so that it is fixed on the rack, relative to frame 1, by means of first setting screw 25. To guarantee the displacement of first clamping plate 21, the latter has a first oblong hole 26, through which first setting screw 25 passes. The other end of first leaf spring 2, not shown, is attached to frame 1 so that it is fixed on the rack.

Figure 6:
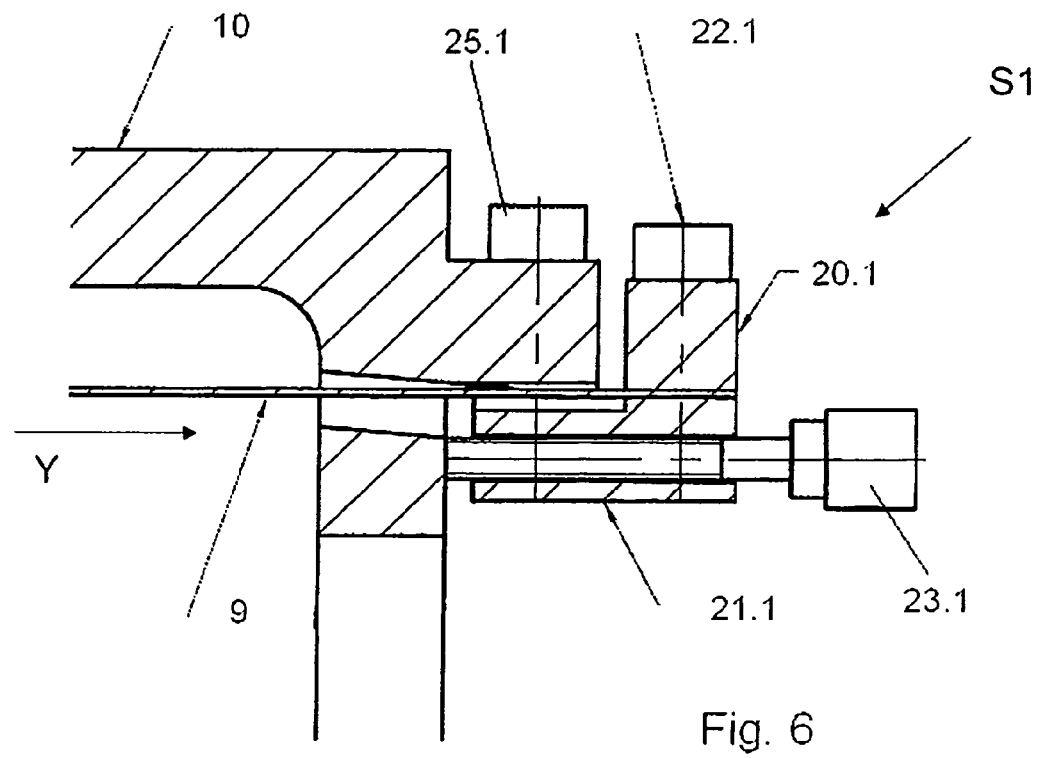
FIG. 6 shows a cross sectional view of an embodiment of the invention with a second leaf spring on the rack.
Figure 7:
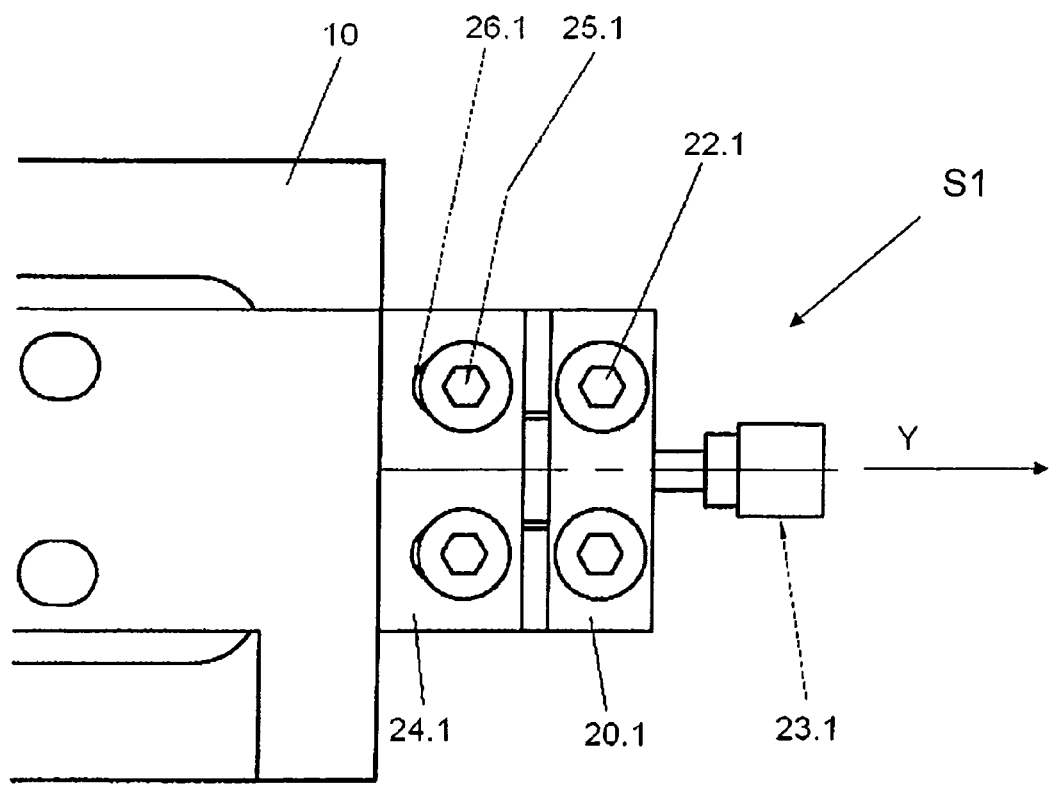
FIG. 7 shows a top view of the embodiment shown in FIG. 6.

FIGS. 6 and 7 show an embodiment using a second leaf spring 9 attached on rack 10 in a cross-sectional view and a top view, respectively.

Second bracing element S1, which can generate a bias of second leaf spring 9 in the Y direction similar to the aforementioned embodiment, includes second clamping strap 20.1, second clamping plate 21.1, second adjusting screw 22.1, and second straining screw 23.1. One end of second leaf spring 9 is clamped in place between second clamping strap 20.1 and second clamping plate 21.1, by means of second adjusting screw 22.1. Second clamping plate 21.1 is braced against rack 10 by means of second straining screw 23.1, biasing second leaf spring 9 in its longitudinal direction (Y direction) when second straining screw 23.1 is tightened. Second clamping plate 21.1 can be screwed on tightly, relative to rack 10, by means of second setting screw 25.1, so that it is fixed on the rack. To guarantee the displacement of second clamping plate 21.1, the latter has a second oblong hole 26.1, through which second setting screw 25.1 passes. The other end of second leaf spring 9, not shown, is attached to frame 1 so that it is fixed on the rack.

Aside from the exemplary embodiments described, other arrangements and mountings are also possible, but the principle according to the invention for measuring force and displacement remains the same. For example, the number of leaf springs can vary, or the suspension can be provided in a different manner (e.g. spiral springs).

What is claimed is:

1. A device for high precision generation and measurement of forces and displacements along a single axis X, having great rigidity in an axis Y perpendicular to the axis X, the device comprising:
   a) a shaft for transferring the forces;
   b) at least two first leaf springs attached to said shaft, wherein said at least two first leaf springs are clamped at each end and biased in a direction toward the axis Y;
   c) a first closed frame movably mounted to a rack with at least two second leaf springs, wherein said at least two first leaf springs are clamped in said closed frame; and
   d) a first bracing element for adjusting a bias of said at least two first leaf springs said first bracing element comprising
   a first clamping strap;
   a first clamping plate;
   a first adjusting screw for clamping a first end of one of said at least two first leaf springs between said first clamping strap and said first clamping plate; and
   a first straining screw for adjusting said first clamping plate against said closed frame in a direction along the axis Y to bias said leaf spring clamped between said first clamping strap and said first clamping plate in a longitudinal direction along the axis Y.

2. The device according to claim 1, wherein said at least two first leaf springs comprise at least one double pair of first leaf springs clamped at each end.

3. The device according to claim 1, wherein said at least two first leaf springs are deflected in a direction along the axis X.

4. The device according to claim 1, wherein said at least two second leaf springs comprise at least one double pair of second leaf springs.

5. The device according to claim 1, wherein said at least two second leaf springs are deflected in a direction along the axis X.

6. The device according to claim 1, wherein said closed frame is mounted to said rack with four third leaf springs, wherein each of said four third leaf springs is clamped at one end.

7. The device according to claim 6, wherein said four third leaf springs are deflected in a direction along the axis X.

8. The device according to claim 1, further comprising a movement element for moving said closed frame in a direction along said axis X, and a connecting shaft coupling said movement element to said closed frame.

9. The device according to claim 8, wherein said movement element comprises a piezoelectric element.

10. The device according to claim 1, further comprising a device for measuring force coupled to said shaft.

11. The device according to claim 10, wherein said device for measuring force measures the force optically.

12. The device according to claim 1, further comprising a device for measuring a path coupled to said shaft.

13. The device according to claim 12, wherein said device for measuring a path measures the path optically.

14. The device according to claim 1, further comprising a device for measuring force coupled to said shaft and a device for measuring a path coupled to said shaft.

15. The device according to claim 14, wherein said device for measuring force comprises a first LVDT and said device for measuring path comprises a second LVDT.

16. The device according to claim 1, wherein the measurement of forces is derived from displacement of said shaft.

17. The device according to claim 1, further comprising a clamping element for attaching a second end of said one of said at least two first leaf springs to said closed frame.

18. The device according to claim 1, further comprising a second bracing element for adjusting a bias of said at least two second leaf springs in a direction along the axis Y.

19. The device according to claim 18, wherein said second bracing element comprises:
   a second clamping strap;
   a second clamping plate;
   a second adjusting screw for clamping a first end of one of said at least two second leaf springs between said second clamping strap and said second clamping plate; and
   a second straining screw for adjusting said second clamping plate against said rack to bias said leaf spring clamped between said second clamping strap and said second clamping plate in a longitudinal direction along the axis Y.

20. The device according to claim 19, further comprising a clamping element for attaching a second end of said one of said at least two second leaf springs to said closed frame.

* * * * *